United States Patent [19]

Kingsbury

[11] Patent Number: 5,257,527
[45] Date of Patent: Nov. 2, 1993

[54] METHOD AND APPARATUS FOR MEASURING COMPONENTS OF AN AMBIENT FLUID

[76] Inventor: Alan P. Kingsbury, 246 Millerton Rd., Sharon, Conn. 06069

[21] Appl. No.: 723,167

[22] Filed: Jun. 28, 1991

[51] Int. Cl.$^5$ .................... G01N 1/14; G01N 1/24; G01N 30/16
[52] U.S. Cl. .................... 73/31.01; 73/23.41; 73/864.15; 73/864.16
[58] Field of Search .......... 73/864.87, 864.62, 864.73, 73/864.74, 31.01, 31.02, 23.41, 61.55, 64.56, 864.15, 864.16, 864.21, 864.22, 864.34, 864.35

[56] References Cited

U.S. PATENT DOCUMENTS

| | | | |
|---|---|---|---|
| 944,247 | 12/1909 | Smith | 73/23.2 X |
| 1,458,893 | 6/1923 | Rodhe | 73/23.2 X |
| 2,218,899 | 10/1940 | Warren | 73/864.15 |
| 2,284,147 | 5/1942 | Herrick | 73/864.73 X |
| 2,386,832 | 10/1945 | Zeikowsky et al. | 73/864.73 X |
| 2,728,232 | 12/1955 | Bremmer | 73/864.15 |
| 2,991,647 | 7/1961 | Harris | 73/23.35 X |
| 3,167,947 | 2/1965 | Crawford | 73/23.35 |
| 3,246,559 | 4/1966 | Clifford, Jr. | 73/864.15 X |
| 3,471,692 | 10/1969 | Llewellyn et al. | 73/23.41 X |
| 4,507,955 | 4/1985 | Haase | 73/61.65 |

OTHER PUBLICATIONS

Sensidyne Catalog, by Sensidyne, Inc. of Clearwater, Fla., pg. bearing notation "Rev. 4-91" on an un-numbered page; p. 13 of catalog also enclosed.

*Primary Examiner*—Tom Noland
*Attorney, Agent, or Firm*—Nolte, Nolte and Hunter

[57] ABSTRACT

A system for measuring components of an ambient fluid such as air. A syringe includes an intake fitting which provides sealed fluid coupling to a chromatographic intake tube. The syringe includes exhaust ports near the intake end of the syringe. The ports exhaust fluid in the cylinder directly into the atmosphere without passing the exhaust fluid through the indicator tube. The exhaust ports are shaped and located to be sealed by the thumb and forefinger of an operator's hand. In operation, the operator covers the exhaust ports on the syringe with his fingers. He then pulls the plunger to draw fluid into the syringe. He then withdraws his fingers to open the vent holes and expells fluid through the vent holes by depressing the plunger. These steps are repeated until a preselected volume of fluid has been drawn syringe-ward through the analysis tube. The tube is then observed.

2 Claims, 1 Drawing Sheet

METHOD AND APPARATUS FOR MEASURING COMPONENTS OF AN AMBIENT FLUID

FIELD OF INVENTION

This invention relates to a method and apparatus for drawing a fluid such as ambient air through a chemical sampling tube in order to facilitate analysis in such a tube.

BACKGROUND OF THE INVENTION

In the past few years public attention has been drawn to the fact that modern energy efficient sealed buildings often recycle air, through poorly maintained duct systems to such a degree that the air eventually may become unhealthy. Contaminates in carpets and fibers, paints, inks, copying machinery, smoke, and/or radon emissions, may collect in the ambient air of a building to concentrations that may have adverse affects on the health of the building's occupants.

In order to determine the extent of such contamination, it is useful to provide means of analyzing the air for the presence of these various contaminants.

For some time now, there has been available simple glass tubes filled with chromatographic material. The chromatographic material reacts to the presence of specific contaminants in the ambient air by changing color. Such color changes provide qualitative and/or quantitative measurements of the concentrations of these contaminants.

In order to provide specific results from these chromatographic tubes, it is necessary to draw measured quantities of air through the chromatographic material. It is the object of this invention to provide a simple and inexpensive device for measuring and propelling the quantities of air which are drawn through such a tube.

BRIEF DESCRIPTION OF THE INVENTION

The invention comprises a syringe of appropriate volume. An intake fitting is provided for coupling the syringe in fluid communication with the chromatographic sampling tube. One or two holes are provided in the cylindrical wall of the syringe near the intake fitting for venting the syringe.

In operation, the operator draws back the plunger while covering the vent holes with his fingers. This draws a fluid such as ambient air through the chromatographic analysis tube. Since the volume containable in the syringe may be insufficient to provide sufficient gas flow through the chromatographic tube to achieve proper analysis, the fingers are then removed from the vent holes and the plunger is driven back toward the intake, forcing the piston to expel air through the vent holes. When the piston has been fully displaced toward the intake, the fingers again cover the vent holes and the piston is drawn back by the plunger which draws air through the analysis tube. The procedure is repeated until sufficient air has been drawn through the tube to provide a proper analysis. The amount of air drawn through the tube is easily calculated by multiplying the volume of the syringe times the number of strokes.

DETAILED DESCRIPTION OF THE DRAWINGS

Figure 1A:
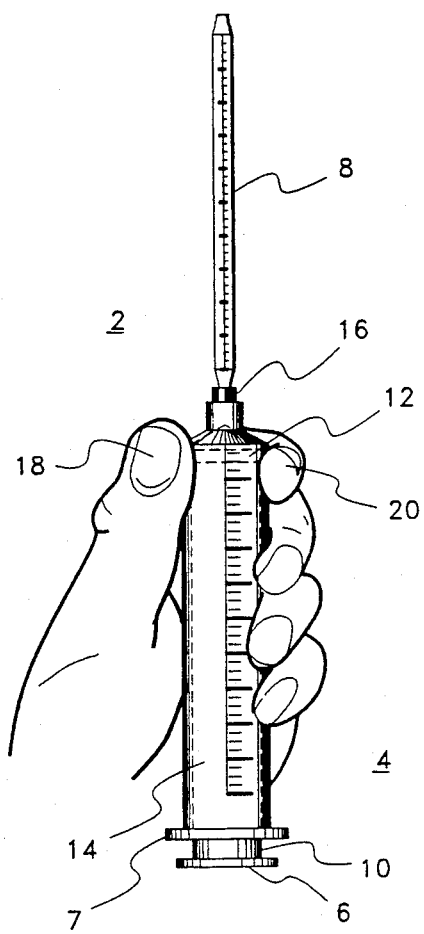
FIG. 1A hereafter referred to as FIG. 1 is an elevation of the apparatus of the present invention showing the operator's fingers covering the vent holes.

FIG. 1 shows the apparatus, generally designated 2. It comprises a syringe, generally designated 4, which includes a plunger 6. The purpose of syringe 4 is to draw fluid, such as ambient air, through a workpiece which is intended to be a gas chromatography tube such as tube 8. It is envisioned that for proper operation of analysis tube 8, a volume of air equal to several volumes of the syringe should be drawn through tube 8. In operation then, plunger 6 is depressed to near flange 7 driving rod 10 and consequently piston 12 toward the intake end of hollow cylinder 14, which is preferably graduated. Intake fitting 16 provides fluid communication with analysis tube 8. Thumb 18 and forefinger 20 cover a pair of vent holes 22, 24, shown in FIG. 2.

From the instructions accompanying tube 8, the operator determines how much air should be drawn through the tube 8 and divides that volume by the maximum volume of cylinder 14. The answer is the number of full strokes which the operator must take to pass this amount of fluid through tube 8. Tube 8 is fitted to fitting 16 which provides sealed fluid communication with syringe 4.

Figure 2:
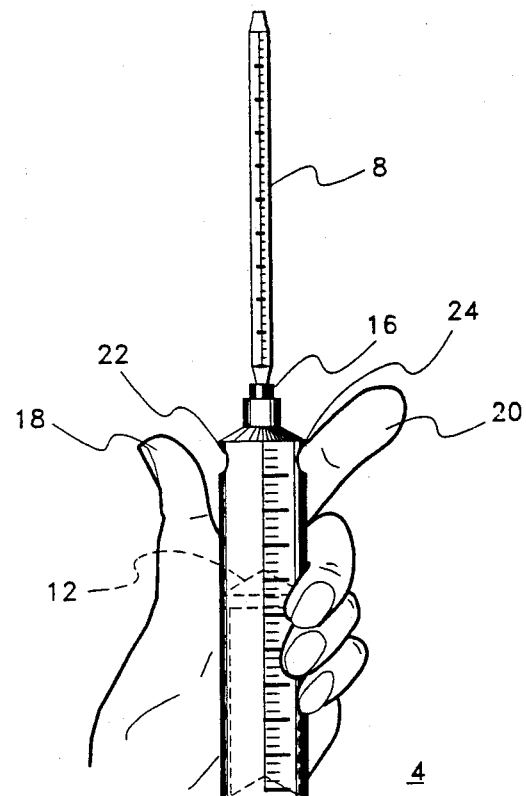
FIG. 2 is a similar elevation showing the vent holes uncovered by the fingers and showing the plunger in phantom lines partially extended and in black lines fully extended.

In operation, thumb 18 and forefinger 20 are left in place over vent holes 22 and 24, as in FIG. 1, and plunger 6 is drawn away from the intake, as in FIG. 2, drawing a partial vacuum behind piston 12 and drawing air through tube 8. FIG. 2, with piston 12 at its full extent, piston 12 has displaced the maximum volume of air into cylinder 14 through tube 8. Thumb 18 and forefinger 20 then uncover holes 22 and 24 as in FIG. 2 and plunger 6 is again driven home toward the intake 16. Most of the air in cylinder 14 is expelled through the now open vent holes 22 and 24. Such expulsion makes measurement in the tube more accurate, because many of the contaminants in the drawn air in the cylinder 14 will have already reacted with the chromatographic materials in tube 8. Thus, the concentration of contaminants in the air expelled from the syringe will be less than the concentration of contaminants in the ambient air, thus introducing a degree of imprecision to the measurements if such air is expelled through the tube. Accordingly, it can be seen that it is necessary to exhaust such air through vent holes 20 and 24.

When piston 12 is at the intake-ward end of the cylinder, thumb 18 and forefinger 20 again cover vent holes 22 and 24 and the intake stroke is repeated. These operations are repeated the number of times desired as calculated above.

Figure 3:
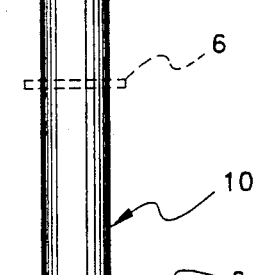
FIG. 3 is an elevation of a portion of FIG. 2, turned 90°, showing the end of the syringe of the present invention with the vent holes and the intake fitting in greater detail.
Figure 3:
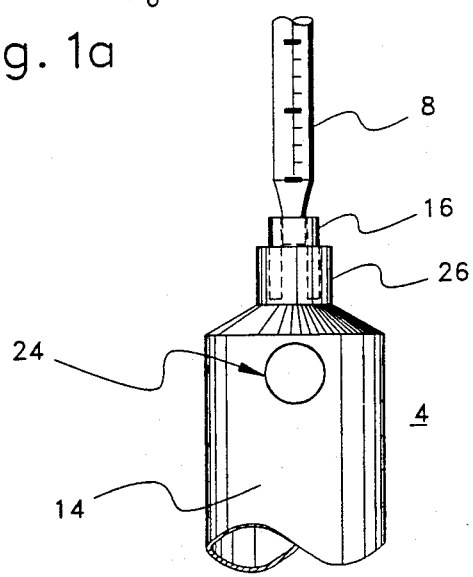

FIG. 3, detail "A" shows how intake fitting 16 is snugly nested inside nozzle 26. Tube 8 is fitted into fitting 16 to provide fluid communication between syringe 4 and tube 8. Intake fitting 16 is preferably a length of flexible, resilient tubing such as tygon tubing, selectively sized to fit snugly into nozzle 26 in a fluidly sealed relationship.

Having thus described my invention, I claim:

1. A method of analyzing a fluid comprising the steps of:

covering an exhaust port on a syringe coupled to an analysis tube, said exhaust port being located near a fluid intake end of the syringe;

drawing a piston within the syringe in a direction expanding the volume on the intakeward side of the piston to draw fluid through the analysis tube;

uncovering the exhaust port by withdrawing a surface of an operator's hand therefrom;

driving the piston into the syringe to expel the fluid therefrom through the exhaust port;

repeating the above steps until a preselected volume of fluid has been drawn syringe-ward through the analysis tube; and observing an effect of the operation on the analysis tube.

2. A method according to claim 1 in which the fluid drawn into the analysis tube is ambient air.

* * * * *